US008158134B1

(12) United States Patent
Supersaxo et al.

(10) Patent No.: US 8,158,134 B1
(45) Date of Patent: Apr. 17, 2012

(54) MICROEMULSION PRECONCENTRATE, MICROEMULSION AND USE THEREOF

(75) Inventors: Andreas Supersaxo, Baar (CH); Marc Antoine Weder, Rüschlikon (CH); Hans Georg Weder, Rüschlikon (CH)

(73) Assignee: Vesifact AG, Baar (CH)

(*) Notice: Subject to any disclaimer, the term of this patent is extended or adjusted under 35 U.S.C. 154(b) by 1463 days.

(21) Appl. No.: 10/110,212

(22) PCT Filed: Oct. 20, 2000

(86) PCT No.: PCT/CH00/00569
§ 371 (c)(1),
(2), (4) Date: Apr. 19, 2002

(87) PCT Pub. No.: WO01/28520
PCT Pub. Date: Apr. 26, 2001

(30) Foreign Application Priority Data

Oct. 20, 1999 (CH) .................................... 1912/99

(51) Int. Cl.
*A61K 9/00* (2006.01)
*A61K 9/46* (2006.01)
*C11D 17/00* (2006.01)

(52) U.S. Cl. ......... 424/400; 424/466; 510/407; 510/421
(58) Field of Classification Search ................. 424/439, 424/466, 401; 510/407, 421
See application file for complete search history.

(56) References Cited

U.S. PATENT DOCUMENTS

| | | | | |
|---|---|---|---|---|
| 4,732,576 A | * | 3/1988 | Friedrich et al. | 44/301 |
| 5,118,493 A | * | 6/1992 | Kelley et al. | 514/11 |
| 5,190,748 A | * | 3/1993 | Bachynsky et al. | 424/78.08 |
| 5,925,684 A | * | 7/1999 | Schweikert et al. | 514/458 |
| 5,929,030 A | * | 7/1999 | Hamied et al. | 514/9 |
| 5,932,243 A | * | 8/1999 | Fricker et al. | 424/450 |
| 5,952,373 A | * | 9/1999 | Lanzendorfer et al. | 514/456 |
| 5,965,115 A | * | 10/1999 | Bolich et al. | 424/70.12 |
| 5,968,495 A | * | 10/1999 | Bolich et al. | 424/70.12 |
| 6,063,762 A | * | 5/2000 | Hong et al. | 514/11 |
| 6,667,044 B1 | * | 12/2003 | Diec et al. | 424/401 |
| 6,765,020 B2 | * | 7/2004 | Yoshimura et al. | 514/558 |
| 2009/0202596 A1 | * | 8/2009 | Pedrani et al. | 424/400 |

FOREIGN PATENT DOCUMENTS

| | | | |
|---|---|---|---|
| WO | WO 93 18852 | | 9/1993 |
| WO | WO 98/15254 | * | 4/1998 |
| WO | WO 99 29300 | | 6/1999 |
| WO | WO 99/29316 | * | 6/1999 |
| WO | WO 99/44642 | * | 9/1999 |
| WO | WO 99 49848 | | 10/1999 |
| WO | WO-99/56727 | * | 11/1999 |
| WO | WO 99 56727 | | 11/1999 |
| WO | WO 99/56727 | * | 11/1999 |

OTHER PUBLICATIONS

John Klier, "Microemulsions," Standard Article, Kirk-Othmer Encyclopedia of Chemical Technology, copyright 1999-2008, abstract.*
Forster et al. "Influence of microemulsion phases on the preparation of fine disperse emulsions," in Advances in Colloid and Interface Science, vol. 58, No. 2, Jul. 12, 1995, pp. 119-149.*
Devani et al. "The development and charcterisation of triglycerided-based 'spontaneous' multiple emulsions," in International Journal of Pharmaceutics 300 (2005) 76-88.*
Koga et al. "Enhancing mechanism of Labrasol on intestinal membrane permeability of the hydrophilic drug gentamicin sulfate," in the European Journal of Pharmaceutics and Biopharmaceutics, Vo. 64, 2006, pp. 82-91.*

* cited by examiner

*Primary Examiner* — Blessing Fubara
(74) *Attorney, Agent, or Firm* — Shoemaker and Mattare

(57) ABSTRACT

The invention relates to compositions in the form of microemulsion preconcentrates that contain (a) a mixture that consists of a medium-chain triglyceride and an omega-9 fatty acid and/or an omega-6 fatty acid; and (b) a surface-active component that contains a polyoxethylene tenside. When contacted with water or with an aqueous medium these microemulsion preconcentrates form microemulsions. The microemulsions of the O/W type have an average particle size below 150 nm, preferably below 100 nm. The inventive microemulsion preconcentrates and microemulsions are suitable for use as vehicles for substances, namely active agents, that are hardly soluble in water, but soluble in components (a) and/or (b). In the aqueous phase, said microemulsions may contain water-soluble substances.

22 Claims, No Drawings

MICROEMULSION PRECONCENTRATE, MICROEMULSION AND USE THEREOF

BACKGROUND

The present invention relates to a new composition and the use thereof.

In a preferred embodiment form of the present invention there is an active ingredient poorly soluble in water. Cyclosporins are an example of such poorly soluble active ingredients.

Cyclosporins comprise a class of cyclic poly-N-methylated undecapeptides, whose representatives have pharmacological properties, in particular immuno-suppressive, anti-inflammatoric and/or anti-parasitic properties. The most famous of representatives of this class is cyclosporin A which is the active ingredient of the commercially available preparations SANDIMMUN and NEORAL.

Cyclosporins are neutral lipophilic (i.e. hydrophobic) substances with a low water solubility. Formulations of cyclosporins, e.g. for oral administration, are based mainly on the use of ethanol and oils or similar auxiliary agents as carrier media. Thus according to the Journal of Drug Targeting, 1998, Vol. 5, No. 6, pages 443-458 (in particular pages 447 and 448) the commercially available preparation SANDIMMUN is obtainable in three different forms, specifically soft gelatine capsules, containing cylcosporine A, water-free ethyl alcohol (up to 12.7%), Labrafil M 2125 CS (polyoxyethylated glycolisated glycerides), maize oil and further ingredients;

an oral solution, containing cyclosporin A, ethyl alcohol (up to 12.5%), olive oil, Labrafil M 1944 CS (polyoxyethylated oleic acid glyceride); and further ingredients; and an injection preparation, containing cyclosporin A, ethyl alcohol (32.9%) and Cremophor EL (polyethoxylated risinus oil); and the commercially available preparation NEORAL in two forms, specifically soft gelatine capsules, containing cyclosporin A, water-free ethyl alcohol (up to 9.5%), maize oil glycerides, Cremophor RH 40 (polyoxyethylated hydrated risinus oil), propylene glycol and further ingredients; and an oral solution, containing cyclosporin A, water-free ethyl alcohol (up to 9.5%), maize oil glycerides, Cremophor RH 40, propylene glycol and further excipients.

From DE 39 30 928 C2 there are known formulations which contain a cyclosporin as an active ingredient; a hydrophilic phase, specifically a pharmaceutically acceptable $C_1$-$C_5$-alkyl- or tetrahydrofurfuryl-diether or -partial ether of a low-molecular mono- or polyoxy-$C_2$-$C_{12}$-alkanediol, preferably transcutol (diethylene glycol mono ethyl ether) or glycofurol(tetrahydrofufurylalcohol polyethylene glycol ether) and/or 1,2-propylene glycol; a lipophilic phase; and a surface-active agent. The hydrophilic phase may additionally also contain further components, for example lower alkanols, such as ethanol.

From WO 99/00002 A there are known formulations which contain cyclosporin as an active ingredient; a polycarboxylic acid ester and/or a polyolcarboxylic acid ester; an oil; and a surface-active agent. The polycarboxylic acid esters are hereby esterification products of polycarboxylic acids with 2-10, preferably 3-5 carboxyl groups with $C_1$-$C_{10}$ alcohols, such as triethyl citrate, tributyl citrate, acetyltributyl citrate and acetyltriethyl citrate, and the polyolcarboxylic acids are hereby esterification products of polyols with 2-10, preferably 3-5 hydroxyl groups with $C_2$-$C_{11}$-carboxylic acids, such as e.g. triacetine.

SUMMARY OF THE INVENTION

As the above-discussed, known formulations, the formulations according to the present invention are microemulsion preconcentrates or microemulsions.

A microemulsion preconcentrate is to be understood as a system which on contact with water, e.g. with the addition of water, gives a microemulsion. Such a microemulsion is within the conventionally acknowledged meaning, a non-opaque or practically non-opaque colloidal dispersion, which contains water and organic components with the inclusion of lipophilic (i.e. hydrophobic) components.

Micro-emulsions may be recognised in that they have one or more of the following properties:

They are formed spontaneously when their components are brought into contact with one another; for this practically no supply of energy is necessary, and the formation of such microemulsions is therefore effected without heating or the application or a high shear force or other significant through-mixing.

They are practically non-opaque, specifically transparent or opalescent when they are observed under an optical microscope: in their non-disturbed condition they are optically isotropic although when observed for example with the use of X-ray irradiation technology one may ascertain an anisotropic structure.

They contain a disperse or particulate (droplet) phase, whose particles have a size of less than 200 nm, from which their optical transparency originates. The particles may be spherical or have other structures; for example they may be liquid crystals with lamellar, hexagonal or isotropic symmetries. Generally microemulsions contain droplets or particles with a maximal dimension, for example a diameter, of less than 150 nm, usually about 10-100 nm.

The microemulsion preconcentrates according to the invention are accordingly above all systems which contain an active ingredient which is poorly soluble in water, such as a cyclosporin, and which on bringing together with water are spontaneously or practically spontaneously i.e. without significant application of energy, capable of forming a microemulsion.

The microemulsion preconcentrates according to the invention are above all characterised in that they contain
(a) a mixture consisting of a medium-chain tri glyceride and an omega-9 fatty acid and/or an omega-6 fatty acid and
(b) a surface-active component containing a tenside of the polyoxethylene type. Such preconcentrates contain preferably as a component (c) an active ingredient which is poorly soluble in water but soluble in component (a) and/or (b).

In contrast to the formulations according to DE 39 30 928 C2 and WO 99/00002 A they may be essentially free of components which are mixable with water or soluble in water. Such components are in particular
(a) $C_1$-$C_5$-alkyl- or tetrahydrofurfuryl-diethers or -partial ethers of low molecular mono- or polyoxy-$C_2$-$C_{12}$-alkanediols;
(b) 1,2-propylene glycol;
(c) lower alkanols;
(d) esterification products of polycarboxylic acids with 2-10, in particular 3-5 carboxyl groups with $C_1$-$C_{10}$ alcohols; and
(e) esterification products of polyols with 2-10, in particular 3-5 carboxyl groups with $C_2$-$C_{11}$ carboxylic acids;
in particular free of diethylene glycol monomethyl ether, glycofurol, 1,2-propylene glycol, triethyl citrate, tributyl citrate, acetyl tributyl citrate, acetyl triethyl citrate, triacetine, ethanol, polyethylene glycol, dimethyl isosorbite and propylene carbonate.

As component (a) mixtures of a medium-chain fatty acid triglyceride, usefully of a fatty acid triglyceride in which the fatty acid radicals comprise 4-18, preferably 6 to 18 C-atoms, and of an omega-9 and/or omega-6 fatty acid are suitable. These substances are not mixable with water or are insoluble or practially insoluble in water and have no or practically no surface-active function.

Preferred medium-chain fatty acid tri glycerides are caprylic/capric acid triglycerides, as they are known for example under the trade description MIGLYOL and are obtainable on the market (Fiedler, Lexikon der Hilfsstoffe (encyclopaedia of auxilary agents), 3rd edition, pages 808 to 809, 1989). To this belong for example the following products:

MIGLYOL 810
This is a fractionated coconut oil which contains triglycerides of caprylic acid and capric acid and has a molecular weight of about 520. It comprises a fatty acid composition with $C_6$ (maximum 2 percent, $C_8$ (about 65 to 75 percent), $C_{10}$ (about 25 to 35 percent) and $C_{12}$ (maximum 2 percent).

MIGLYOL 812
This is a fractionated coconut oil which contains triglycerides of caprylic acid and capric acid and has a molecular weight of about 520. It comprises a fatty acid composition with $C_6$ (maximum 3 percent), $C_8$ (about 50 to 65 percent), $C_{10}$ (about 30 to 45 percent) and $C_{12}$ (maximum 5 percent).

MIGLYOL 818
These are triglycerides of caprylic acid, capric acid and linoleic acid with a molecular weight of about 510. It comprises a fatty acid composition with $C_6$ (maximum 3 percent), $C_8$ (about 45 to 60 percent), $C_{10}$ (about 25 to 40 percent), $C_{12}$ (about 2 to 5 percent) and $C_{18_2}$ (about 4 to 6 percent).

Furthermore also triglycerides of caprylic acid and capric acid are suitable, as are known and obtainable under the product description MYRITOL (Fiedler, Lexikon der Hilfsstoffe (encyclopaedia of auxilary agents), 3rd edition, page 834, 1989). To these there belongs for example the product MYRITOL 813.

Further suitable products of this class are CAPTEX 355, CAPTEX 300, CAPTEX 800, CAPMUL MCT, NEOBEE M5 and MAZOL 1400.

Suitable omega-9 fatty acids are mainly those with 12-24, in particular 16-24, preferably 18-22 C-atoms, for example oleic acid and eicosatrienic acid. Particularly preferred is oleic acid.

Suitable omega-6 fatty acids are mainly those with 12-24, in particular 16-24, preferably 18-22 C-atoms, for example linoleic acid, gamma-linolenic acid, dihommo-gamma-linoleic acid and arachidonic acid. Particularly preferred is linoleic acid.

In a particularly preferred embodiment form as component (a) one uses a mixture consisting of a caprylic/capric acid-triglyceride, oleic acid and/or linoleic acid.

Component (c), the therapeutic active ingredient which is poorly soluble in water but soluble in component (a) and/or (b) is for example a cyclosporin, preferably cyclosporin A or another suitable cylcosporin, for example another natural cyclosporin; one of the various non-natural cyclosporin derivatives or a synthetic cyclosporin.

Component (b), the surface-active component containing a tenside of the polyoxethylene type, can be a hydrophilic surface-active agent or a lipophilic surface-active agent, but also mixtures of such agents may be considered.

Examples of such tensides are the following:
reaction products of natural or hydrated vegetable oils and ethylene glycol, specifically polyoxyethylene-glycolated natural or hydrated vegetable oils, such as polyoxyethylene-glycolated natural or hydrated risinus oils. Particularly suitable are the various tensides which are known and obtainable under the description CREMOPHOR (Fiedler, Lexikon der Hilfsstoffe (encyclopaedia of auxilary agents), 3rd edition, pages 326 to 327, 1989), above all the products with the descriptions CREMOPHOR RH 40, CREMOPHOR RH 60 and CREMOPHOR EL. Furthermore as such products also the various tensides which are known and obtainable under the description NIKKOL, for example NIKKOL HCO-60 are suitable.

polyoxyethylene sorbitane fatty acid esters, for example the mono- and triauryl ester, the mono- and tripalmityl ester, the mono- and tristearyl ester and the mono- and trioleylester as they are known and obtainable under the description TWEEN (Fiedler, Lexikon der Hilfsstoffe (encyclopaedia of auxilary agents), 3rd edition, pages 1300 to 1304, 1989), for example the products TWEEN 20: polyoxyethylene (20) sorbitane monolaurate,
TWEEN 40: polyoxyethylene (20) sorbitane monopalmitate,
TWEEN 60: polyoxyethylene (20) sorbitane monostearate,
TWEEN 80: polyoxyethylene (20) sorbitane monooleate,
TWEEN 65: polyoxyethylene (20) sorbitane tristearate,
TWEEN 85: polyoxyethylene (20) sorbitane trioleate,
TWEEN 21: polyoxyethylene (4) sorbitane monolaurate,
TWEEN 61: polyoxyethylene (4) sorbitane monostearate, and
TWEEN 81: polyoxyethylene (4) sorbitane monooleate.

Particularly preferred from this class of compounds is TWEEN 80.

polyoxyethylene fatty acid esters, for example the polyoxyethylene stearic fatty acid esters known and obtainable on the market under the description MYRJ (Fiedler, Lexikon der Hilfsstoffe (encyclopaedia of auxilary agents), 3rd edition, page 834, 1989), in particular the product MYRJ 52, as well as also the polyoxyethylene fatty acid ester known and obtainable under the description CETIOL HE (Fiedler, Lexikon der Hilfsstoffe (encyclopaedia of auxilary agents), 3rd edition, page 284, 1989).

copolymerisates of polyoxyethylene and polyoxypropylene, such as those which are for example known under the description PLURONIC and EMKALYX (Fiedler, Lexikon der Hilfsstoffe (encyclopaedia of auxilary agents), 3rd edition, pages 956 to 958, 1989), in particular the product PLURONIC F68.

block copolymerisates of polyoxyethylene and polyoxypropylene, as they are for example known and obtainable under the description POLOXAMER (Fiedler, Lexikon der Hilfsstoffe (encyclopaedia of auxilary agents), 3rd edition, page 959, 1989), in particular the product POLOXAMER 188.

polyethoxylated vitamin E derivatives, in particular the product VITAMIN E TPGS (d-alpha tocoperyl polyethylene glycol 1000 succinate, Eastman).

polyethoxylated hydroxy fatty acid ester, in particular the product SOLUTOL HS 15 (polyoxyethylene-660-hydroxystearate, BASF).

transesterification products of natural vegetable oil glycerides and polyethylene polyols. To these there belong transesterification products of various, for example non-hydrated vegetable oils such as maize oil, kernel oil, almond oil, peanut oil, olive oil and palm oil, as well as of mixtures of these with polyethylene glycols, in particular with those which have an average molecular weight of 200-800. Various such transesterification products are known and obtainable under the description LABRAFIL (Fiedler, Lexikon der Hilfsstoffe (encyclopaedia of auxilary agents), 3rd edition, page 707;

1989); of these the products LABRAFIL M 1944 CS and LABRAFIL M 2130 CS are particularly suitable.

ethylene oxide adducts of sterols and derivatives thereof, for example of cholesterol and derivatives thereof, such as products which are derived from sitosterol, campesterol or stigmasterol, for example of soya sterols and derivatives of these (Fiedler, Lexikon der Hilfsstoffe (encyclopaedia of auxilary agents), 3rd edition, pages 554 and 555; 1989) as they are known and obtainable under the descriptions GENEROL, in particular the products GENEROL 122 E5, 122 E10 and 122 E25.

The microemulsion preconcentrates according to the invention comprise systems which contain a single surface-active agent as well as systems which contain a mixture of two or more surface-active agents, e.g. TWEEN 80+CREMOPHOR RH 40, TWEEN 80+CREMOPHOR RH 40+VITAMIN E TPGS etc.

According to the invention one preferably uses a surface-active component which contains a polyoxyethylene sorbitane fatty acid ester, a polyoxyethylene-glycolated natural or hydrated vegetable oil or mixtures thereof.

The microemulsion preconcentrates according to the invention may also further contain additional substances, such as e.g. antioxidants, thickening agents, odoriferous agents and flavouring agents, colourings, etc.

As antioxidants for example ascorbyl palmitate, butyl hydroxy anisole (BHA), butyl hydroxy toluene (BHT) and tocopherols, e.g. D, L-alpha-tocopherol (vitamin E) are suitable.

As a thickening agent various pharmaceutically acceptable polymeric and inorganic materials are suitable, such as polyacrylate resins and copolymeric polyacrylate resins, as they are for example known and obtainable under the description CARBOPOL and EUDRAGIT (Fiedler, Lexikon der Hilfsstoffe (encyclopaedia of auxilary agents), 3rd edition, pages 254 to 256 or 486 to 487, 1989), in particular the products CARBOPOL 934, 940 and 941 or EUDRAGIT E, L, S, RL and RS.

celluloses and cellulose derivatives, such as methyl cellulose, ethyl cellulose, propyl cellulose, hydroxypropyl cellulose, hydroxypropyl methyl cellulose, cellulose acetate, cellulose acetate phthalate, cellulose acetate succinate and hydroxypropyl methyl cellulose phthalate as well as salts thereof. Examples of such products are the products known and obtainable under the descriptions KLUCEL and METHOCEL (Fiedler, Lexikon der Hilfsstoffe (encyclopaedia of auxilary agents), 3rd edition, pages 688 and 790, 1989), in particular the products KLUCEL LF, MF, GF and HF and METHOCEL K 100, K 15M, K 100M, E 5M, E 15, E 15M and E 100M.

polyvinyl pryrrolidones, including for example poly-N-vinyl pyrrolidones and vinyl pryrrolidone copolymerisates such as vinyl pyrrolidone vinylacetate copolymerisates. Examples of such products are known and obtainable under the description KOLLIDON (described also in the USA as POVIDONE) (Fiedler, Lexikon der Hilfsstoffe (encyclopaedia of auxilary agents), 3rd edition, pages 694 to 696, 1989), in particular the products KOLLIDON 30 and 90.

polyvinyl resins, including for example polyvinyl acetates and polyvinyl alcohols, as well as also other polymeric materials such as tragacanth rubber, rubber arabicum, and alginates, e.g. alginic acid and salts thereof, such as sodium alginate.

inorganic thickening agents, such as attapulgite, bentonite and silicates, including hydrophobic silicon dioxides, such as alkylated, for example methylated silicon dioxide gels, in particular colloidal silicon dioxides as they are known and obtainable under the description AEROSIL (Handbook of Pharmaceutical Excipients, publisher American Pharamaceutical Association/The Pharmaceutical Society of Great Britain, pages 253 to 256, 1986), in particular the products AEROSIL 130, 200, 300, 380, 0, OX 50, TT 600, MOX 80, MOX 170, LK 84 and the methylated AEROSIL R 972.

If it is planned, in particular for the purpose of oral administration, that the compositions according of the invention be suitable end dosage forms for the direct administration, then according to the present invention also pharmaceutical compositions may be provided which contain a therapeutic active ingredient poorly soluble in water but soluble in component (a) and/or (b) and which themselves are microemulsions; in these microemulsions the active ingredient is to be solubilised in a stable manner, wherein over several weeks there are observed no precipitates. For an oral administration microemulsions which one for example obtains by diluting the microemulsion preconcentrates with water or with an aqueous medium, may be applied directly as drink formulations. If there is envisaged a topical or parenteral application then compositions, in which further auxiliary agents may be present, likewise contain water so that there results an aqueous microemulsion in the form of a spray, gel, a paste, a cream, an injection solution, an infusion solution or likewise. Such pharmaceutical compositions in the form of microemulsions are likewise new and the subject-matter of the present invention.

The microemulsions are above all characterised in that they are obtainable by mixing a microemulsion preconcentrate containing (a) a mixture consisting of a medium-chain triglyceride and an omega-9-fatty acid and/or an omega-6 fatty acid;

(b) a surface-active component containing a tenside of the polyoxethylene type;

(c) an active ingredient poorly soluble in water but soluble in component (a) and/or (b), for example a cyclosporin;

(d) with water or with an aqueous medium.

The composition should be essentially free of components which are mixable with water or soluble in water; these are mainly:

(1) $C_1$-$C_5$-alkyl- or tetrahydrofurfuryl-diether or -partial ethers of low molecular mono- or polyoxy-$C_1$-$C_{12}$-alkanediols;

(2) 1,2-propylene glycol;

(3) lower alkanols;

(4) esterification products of polycarboxylic acids with 2-10, in particular 3-5 carboxyl groups with $C_1$-$C_{10}$-alcohols; and (5) esterification products of polyols with 2-10, in particular 3-5 carboxy groups with $C_2$-$C_{11}$-carboxylic acids;

Depending from the quantity of the water present W/O microemulsions, bicontinuous microemulsions or O/W microemulsions are obtained.

The microemulsions according to the invention of the O/W type (oil-in-water) have stability properties as they have been described further above in the context of microemulsions, i.e. in particular that in these microemulsions the active ingredient is solubilised in a stable manner, and over several weeks no precipitate may be observed. The particle size of these microemulsions is smaller than 150 nm, preferably smaller than 100 nm.

The microemulsion preconcentrates and microemulsions according to the invention are suitable as a vehicle for substances poorly soluble in water but soluble in component (a) and/or (b), specifically pharmaceutical, biotechnological and cosmetic active ingredients as well as foodstuff active ingredients and cell or tissue culture active ingredients. The microemulsion preconcentrates according to the invention may also contain active ingredients in a finely dispersed form. In their aqueous phase the microemulsions according to the invention may contain water-soluble substances, e.g. water-soluble active ingredients.

One example of a pharmaceutical active ingredient poorly soluble in water but soluble in component (a) and/or (b) is the capillary therapeutic quercetin. The microemulsion preconcentrates and microemulsions according to the invention may however also serve as a vehicle for other pharmaceutical active ingredients poorly soluble in water but soluble in components (a) and/or (b).

One example of a cosmetic active ingredient poorly soluble in water but soluble in component (a) and/or (b) is the anti-wrinkle agent coenzyme Q10. Flavonoides, UV-filters and vitamins are further examples of cosmetic active ingredients.

Examples of biotechnological active ingredients are peptides and proteins, in particular recombinant proteins.

Foodstuff active ingredients are nutrients which also have a preventative or health use. Examples of such foodstuff active ingredients are omega-3 fatty acids (such as EPA and DHA) and vitamins.

Examples of cell or tissue culture active ingredients are vitamins and retinoids.

Microemulsion preconcentrates and microemulsions which contain active ingredients which are poorly soluble in water but soluble in component (a) and/or (b) may be applied for administration in any suitable manner, for example orally in a shape body or a unit dosage form, in particular a soft or hard gelatine capsule. For this administration the compositions according to the invention have shown to be particularly suitable since an addition of volatile organic solvents, in particular of the commonly used ethanol is not necessary. With the application of volatile organic solvents, by way of the evaporation of the solvent through the outer wall of the shape body, in particular the soft or hard gelatine capsule, the storage stability is negatively influenced and the active ingredient crystalises. The occurrence of these negative effects must be avoided by complicated measures on packaging and storage.

Further suitable forms of administration are for example interparenterally or topically, for example for use on the skin, such as a spray, cream, paste, lotion, gel, ointment, pulp packagings, cataplasma, plasters, skin pads and likewise; or for an ophthalmic application, for example in the form of eye drops, eye lotions and eye gels. Slightly flowable forms may also for example be used for an intralesional injection or be administered rectally, for example as an enema. They are however first of all envisaged for an oral, parental or topical application, wherein in the case of a topical application in particular the application on the skin is considered.

Microemulsion preconcentrates envisaged for oral administration, containing an active ingredient poorly soluble in water but soluble in component (a) and/or (b) may on contact with water form a microemulsion with an average particle size of below 150 nm, preferably below 100 nm. Microemulsions which one for example obtains by diluting the microemulsion preconcentrates with water or with an aqueous medium may be used directly as drink formulations. If there is envisaged a topical or parenteral application, then compositions in which further auxiliary agents may be present likewise contain water, so that there results an aqueous microemulsion in the form of a spray, gel or paste, a cream, an injection solution, an infusion solution or likewise.

Preferred embodiments of the microemulsion preconcentrates and microemulsions according to the invention envisaged for topical, in particular dermal application contain additionally one or more of the following components:

solid hydrocarbons, for example mineral oil gels, such as soft petrolatum or VASELINE, ceresine and solid paraffins, and also waxes, including animal, vegetable and synthetic waxes, such as sperm oil wax, carnauba wax and bee's wax.

liquid hydrocarbons, for example liquid paraffins, and fatty acid esters, such as isopropyl myristate and cetyl palmitate.

non-volatile silicones, including silicone oils and silicon pastes, as well as copolymerisates of silicone and poly-alkylene oxide (Fiedler, Lexikon der Hilfsstoffe (encyclopaedia of auxiliary agents), 3rd edition, pages 1109 and 1110, 1989), in particular the products known and obtainable under the description PIROETHICON.

By way of the application of such additives or of mixtures thereof emulsions may be obtained in liquid or semi-solid form, in dependence of, for example, the requirements for a topical application.

Usefully the compositions envisaged for topical, in particular dermal application additionally contain an antioxidant, such as ascorbyl palmitate, butyl hydroxy anisole (BHA), butyl hydroxy toluene (BHT) and tocopheroles, e.g. D,L-alpha-tocopherole (vitamin E);

an anti-bacterial agent, such as benzyl alcohol, methylparabene, propylparabene, benzalconium chloride, benzoic acid, sorbic acid or chlorobutanol;

a stabilising agent, such as micro-crystalline starch, sodium EDTA, or magnesium sulphate;

an agent for improving the skin penetration, for example 1-dodecylazacycloheptane-2-on which is also known as AZON (Fiedler, Lexikon der Hilfsstoffe (encyclopaedia of auxiliary agents), 3rd edition, page 190, 1989).

A particularly preferred embodiment form of the composition according to the invention envisaged for dermal administration is characterised in that it is obtainable by use of a component (b) containing a polyoxyethylene sorbitane fatty acid ester and/or a polyoxyethylene-glycolated natural or hydrated vegetable oil.

The micro-emulsion preconcentrates according to the invention may be manufactured in that one intimately mixes the individual constituents with one another, where optionally under heating. The micro-emulsion preconcentrates may also be manufactured in that one dissolves the component (b) under stirring, optionally under heating in the component (a), and combines the obtained solution with the component (c) under further stirring.

The microemulsions according to the invention may be manufactured from the microemulsion preconcentrates by diluting with water or other aqueous fluids.

Micro-emulsion preconcentrates according to the invention which are suitable for oral administration are usefully present in a unit dosage form, e.g. in a soft or hard gelatine capsule, and they contain usefully 0.5 to 20, preferably 5-15 percent by weight of an active ingredient poorly in water but soluble in component (a) and/or (b), for example a cyclosporin (component (c)), 9.5 to 70, preferably 20 to 70 percent by weight and further more widely preferred 25 to 65 percent by weight of a mixture consisting of a medium-chain triglyceride and of an omega-9 fatty acid and/or an omega-6 fatty acid (component (a)) and 20 to 90, preferably 25 to 65 percent by weight of the surface-active component (b).

Microemulsion preconcentrates according to the invention, which are suitable for topical or parenteral application usefully contain 0.01 to 15 percent by weight of an active ingredient poorly soluble in water but soluble in component (a) and/or (b), for example a cyclosporin.

In the cyclosporin compositions according to the invention the quantity ratio of omega-9 fatty acids and/or omega-6 fatty acids to the active ingredient is in particular 0.5:1, preferably at least 1:1. In other cases of active ingredients poorly soluble in water but soluble in component (a) and/or (b) the above quantity ratio may be smaller than 0.5:1.

DESCRIPTION OF THE PREFERRED EMBODIMENTS

By way of the following examples the compositions according to the invention are explained further. The examples 1.1 to 1.22 show the manufacture of cyclosporin compositions in oral unit dosage forms, which for example are suitable for the prevention of rejection of transplants or for the treatment of autoimmune diseases. Examples 2.1 to 2.4 show the manufacture of cyclosporin compositions for a topical application which for example are suitable for the treatment of atopical dermatitis or contact dermatitis, psoriasis, balding or certain eye disenses such as conjunctivitis, uveitis or ceratitis. Example 3.1 shows the manufacture of a cylcosporin composition for a parenteral application which is for example suitable for the prevention of a rejection of transplants.

The examples are described with particular reference to cyclosporin A. By way of application of other suitable active ingredients, in particular also other cyclosporins, however comparable compositions may be manufactured.

Example 4 shows the manufacture of a cyclosporin-placebo microemulsion preconcentrate for the oral application and of a cyclosporin placebo 0/W microemulsion for the topical or parenteral application.

Example 5 shows the manufacture of a quercetin microemulsion preconcentrate for oral application as well as the manufacture of a quercetin O/W-microemulsion for the topical or parenteral application

EXAMPLE 1

The Manufacture of Oral Cyclosporin A Dosage Forms of the Microemulsion Preconcentrate Type

| Example 1.1 | |
|---|---|
| cyclosporin A (c) | 10.00% |
| Miglyol 812 (a1) | 35.00% |
| oleic acid (a2) | 10.00% |
| Tween 80 (b1) | 33.75% |
| Cremophor RH 40 (b2) | 11.25% |

The cyclosporin A is dissolved under stirring at room temperature is dissolved in the components a1 and a2, and the obtained solution is combined under further heating is displaced with the components b1 and b2. The formed microemulsion preconcentrate is filled into a soft or hard gelatine capsule. Hard gelatine capsules are preferably sealed using the quasi-seal-method. Alternatively the micoemulsion preconcentrate may also be filled into a dispenser. In this case the patient by way of a suitable dilution with water or another aqueous fluid from the microemulsion preconcentrate creates an oral drinking solution of the type O/W microemulsion.

In an analogous manner also the following compositions may be manufactured and filled into capsules or into dispensers.

| Example 1.2 | |
|---|---|
| cyclosporin A (c) | 10.00% |
| Miglyol 812 (a1) | 30.00% |
| oleic acid (a2) | 15.00% |
| Tween 80 (b1) | 33.75% |
| Cremophor RH 40 (b2) | 11.25% |

| Example 1.3 | |
|---|---|
| cyclosporin A (c) | 10.00% |
| Miglyol 812 (a1) | 27.50% |
| oleic acid (a2) | 17.50% |
| Tween 80 (b1) | 33.75% |
| Cremophor RH 40 (b2) | 11.25% |

| Example 1.4 | |
|---|---|
| cyclosporin A (c) | 10.00% |
| Miglyol 812 (a1) | 25.00% |
| oleic acid (a2) | 20.00% |
| Tween 80 (b1) | 33.75% |
| Cremophor RH 40 (b2) | 11.25% |

| Example 1.5 | |
|---|---|
| cyclosporin A (c) | 12.50% |
| Miglyol 812 (a1) | 32.50% |
| oleic acid (a2) | 10.00% |
| Tween 80 (b1) | 33.75% |
| Cremophor RH 40 (b2) | 11.25% |

| Example 1.6 | |
|---|---|
| cyclosporin A (c) | 12.50% |
| Miglyol 812 (a1) | 27.50% |
| oleic acid (a2) | 15.00% |
| Tween 80 (b1) | 33.75% |
| Cremophor RH 40 (b2) | 11.25% |

| Example 1.7 | |
|---|---|
| cyclosporin A (c) | 15.00% |
| Miglyol 812 (a1) | 25.00% |
| oleic acid (a2) | 15.00% |
| Tween 80 (b1) | 33.75% |
| Cremophor RH 40 (b2) | 11.25% |

| Example 1.8 | |
|---|---|
| cyclosporin A (c) | 10.00% |
| Miglyol 812 (a1) | 30.00% |
| oleic acid (a2) | 15.00% |
| Tween 80 (b1) | 33.75% |
| Cremophor RH 40 (b2) | 11.25% |

| Example 1.9 | |
|---|---|
| cyclosporin A (c) | 10.00% |
| Miglyol 812 (a1) | 35.00% |
| linoleic acid (a2) | 10.00% |
| Tween 80 (b1) | 33.75% |
| Cremophor RH 40 (b2) | 11.25% |

| Example 1.10 | |
|---|---|
| cyclosporin A (c) | 10.00% |
| Miglyol 812 (a1) | 30.00% |
| linoleic acid (a2) | 15.00% |
| Tween 80 (b1) | 33.75% |
| Cremophor RH 40 (b2) | 11.25% |

| Example 1.11 | |
|---|---|
| cyclosporin A (c) | 12.50% |
| Miglyol 812 (a1) | 27.50% |
| linoleic acid (a2) | 15.00% |
| Tween 80 (b1) | 33.75% |
| Cremophor RH 40 (b2) | 11.25% |

| Example 1.12 | |
|---|---|
| cyclosporin A (c) | 15.00% |
| Miglyol 812 (a1) | 25.00% |
| linoleic acid (a2) | 15.00% |

-continued

| | |
|---|---|
| Tween 80 (b1) | 33.75% |
| Cremophor RH 40 (b2) | 11.25% |

Example 1.13

| | |
|---|---|
| cyclosporin A (c) | 10.00% |
| Miglyol 812 (a1) | 30.00% |
| oleic acid (a2) | 15.00% |
| Tween 80 (b1) | 25.00% |
| Cremophor RH 40 (b2) | 10.00% |
| vitamin E TGPS (b3) | 10.00% |

Example 1.14

| | |
|---|---|
| cyclosporin A (c) | 10.00% |
| Miglyol 812 (a1) | 25.00% |
| oleic acid (a2) | 15.00% |
| Tween 80 (b1) | 33.75% |
| Cremophor EL (b2) | 11.25% |

Example 1.15

| | |
|---|---|
| cyclosporin A (c) | 10.00% |
| Miglyol 812 (a1) | 25.00% |
| oleic acid (a2) | 15.00% |
| Tween 80 (b1) | 33.75% |
| Cremophor EL (b2) | 11.25% |

Example 1.16

| | |
|---|---|
| cyclosporin A (c) | 10.00% |
| Miglyol 812 (a1) | 30.00% |
| oleic acid (a2) | 15.00% |
| Tween 80 (b1) | 25.00% |
| Cremophor RH 40 (b2) | 10.00% |
| Labrafil M 1944 CS (b3) | 10.00% |

Example 1.17

| | |
|---|---|
| cyclosporin A (c) | 10.00% |
| Miglyol 812 (a1) | 30.00% |
| oleic acid (a2) | 15.00% |
| Tween 80 (b1) | 22.50% |
| Cremophor RH 40 (b2) | 22.50% |

Example 1.18

| | |
|---|---|
| cyclosporin A (c) | 10.00% |
| Miglyol 812 (a1) | 30.00% |
| linoleic acid (a2) | 15.00% |
| Tween 80 (b1) | 22.50% |
| Cremophor EL (b2) | 22.50% |

Example 1.19

| | |
|---|---|
| cyclosporin A (c) | 10.00% |
| Miglyol 812 (a1) | 29.80% |
| oleic acid (a2) | 15.00% |
| Tween 80 (b1) | 33.75% |
| Cremophor RH 40 (b2) | 11.25% |
| D,L-alpha-tocopherol*[)] | 0.20% |

Example 1.20

| | |
|---|---|
| cyclosporin A (c) | 10.00% |
| Miglyol 812 (a1) | 29.95% |
| oleic acid (a2) | 15.00% |
| Tween 80 (b1) | 33.75% |
| Cremophor RH 40 (b2) | 11.25% |
| ascorbyl palmitate*[)] | 0.05% |

Example 1.21

| | |
|---|---|
| cyclosporin A (c) | 5.00% |
| Miglyol 812 (a1) | 40.00% |
| oleic acid (a2) | 10.00% |
| Tween 80 (b1) | 33.75% |
| Cremophor RH 40 (b2) | 11.25% |

Example 1.22

| | |
|---|---|
| cyclosporin A (c) | 2.50% |
| Miglyol 812 (a1) | 42.50% |
| oleic acid (a2) | 10.00% |
| Tween 80 (b1) | 33.75% |
| Cremophor RH 40 (b2) | 11.25% |

*[)]antioxidant

If compositions of the above type are diluted with water or another aqueous medium e.g. to 1:100, there arise microemulsions which in the case of representative examples have the following particle sizes:

| Composition | O/W-microemulsion | |
|---|---|---|
| Microemulsion preconcentrate | particle size diameter[1)] [nm] | standard deviation[1)] [nm] |
| Example 1.1 | 29.0 | 14.0 |
| Example 1.2 | 31.7 | 12.0 |
| Example 1.3 | 32.0 | 12.3 |
| Example 1.4 | 68.3 | 30.7 |
| Example 1.5 | 29.5 | 13.0 |
| Example 1.6 | 52.3 | 25.6 |
| Example 1.7 | 81.6 | 55.4 |
| Example 1.10 | 34.1 | 10.0 |
| Example 1.13 | 67.7 | 31.0 |
| Example 1.14 | 34.7 | 9.6 |
| Example 1.19 | 32.6 | 12.1 |
| Example 1.20 | 31.9 | 11.5 |

[1)]The particle diameter and particle size distribution (Gauss) are determined by way of laser laserlight scattering (Nicomp 370 Submicron particles Sizer, Volume weighting).

(1) The particle diameter and particle size distribution (Gauss) are determined by way of laser laserlight scattering (Nicomp 370 Submicron particles Sizer, Volume weighting).

From the subsequent table it is evident that in the case of representative examples the cyclosporin A microemulsions formed from the microemulsion preconcentrates with respect to particle size and distribution have an excellent storage stability. Furthermore during this storage one observes no cyclosporin A precipitates.

| Composition | O/W microemulsion | | | |
|---|---|---|---|---|
| | Storage conditions | | particle | standard |
| Microemulsion preconcentrate | time [months] | temp. [° C.] | diameter[1)] [nm] | deviation[1)] [nm] |
| Example 1.19 | 0 | | 32.6 | 12.1 |
| | 1 | 7 | 4.6 | 13.3 |
| | 1 | 25 | 35.5 | 13.4 |
| | 1 | 40 | 37.5 | 13.3 |
| Example 1.20 | 0 | | 31.9 | 11.5 |
| | 1 | 7 | 33.6 | 14.0 |
| | 1 | 25 | 35.9 | 14.3 |
| | 1 | 40 | 36.4 | 13.9 |

[1)]The particle diameter and particle size distribution (Gauss) are determined by way of laser laserlight scattering (Nicomp 370 Submicron particles Sizer, Volume weighting).

(1) The particle diamater and particle size distribution (Gauss) are determined by way of laser laserlight scattering (Nicomp 370 Submicron particles Sizer, Volume weighting).

EXAMPLE 2

The Manufacture of Topically Applicable Cyclosporin A Forms of the Microemulsion Type The microemulsion preconcentrates described in example 1.1 to 1.22 subsequently serve as a basis for manufacturing sprays, gels, creams and other topical administration forms in that the are further combined with further additives such as water, thickening agents and likewise.

| Example 2.1: Cylcosporine A 0.25% microemulsions pump spray | |
|---|---|
| Microemulsion preconcentrate according to Example. 1.21 | 5.00% |
| Na$_2$-EDTA | 0.10% |
| benzalkonium chloride | 0.01% |
| 10 mM phosphate buffer pH 6 | ad 100.00% |

The microemulsion preceoncentrate is added under stirring at room temperature to the phosphate buffer, containing Na$_2$-EDTA and benzalkonium chloride. The resulting cyclosporin A O/W microemulsion is filled into a pump spray. Instead of the pump spray also pressurised gas and aerosol sprays may be considered.

| Example 2.2: Cyclosporin A 0.25% hydrogel | |
|---|---|
| Microemulsion preconcentrate according to Example 1.2 | 2.50% |
| Na$_2$-EDTA | 0.10% |
| benzalkonium chloride | 0.01% |
| sodium carboxymethyl cellulose 450 cp | 3.50% |
| 10 mM phosphate buffer pH 6 | ad 100.00% |

The microemulsion preconcentrate is added under stirring is added to the phosphate buffer, containing Na$_2$-EDTA and benzalkonium chloride. The resulting cyclosporin A O/W microemulsion is processed and manufactured in the usual manner with the sodium carboxylmethyl cellulose into the hydrogel.

| Example 2.3: Cyclosporin A 0.25% O/W emulsion | |
|---|---|
| Microemulsion preconcentrate according to Example. 1.10 | 2.500% |
| isopropyl palmitate | 8.000% |
| glyceryl stearate | 7.000% |
| glycerine | 5.000% |
| stearath-2 + PEG-8 distearate | 4.000% |
| paraffinum liquidum | 4.000% |
| cera microcristallina | 4.000% |
| steareth-21 | 3.000% |
| dimethicon | 1.000% |
| benzyl alcohol | 0.800% |
| phenoxy ethanol | 0.800% |
| lanolin alcohol | 0.100% |
| sodium hydroxide | 0.005% |
| water | ad 100.000% |

The microemulsion preconcentrate is added and mixing to the water phase at room temperature. The resulting cyclosporin A O/W emulsion is processed further and manufactured in the usual manner with the oil phase.

| Example 2.4: Cyclosporin eye drops | |
|---|---|
| Microemulsion preconcentrate according to Example. 1.22 | 4.00% |
| Na$_2$-EDTA | 0.10% |
| benzalkonium chloride | 0.01% |
| isotonic sodium chloride phosphate buffer pH 7.4 | ad 100.00% |

The microemulsion precocentrate is added under stirring at room temperature to the sodium chloride phosphate buffer, containing Na$_2$-EDTA and benzalkonium chloride. The resulting cylcosporin O/W microemulsion is 0.2 μm sterile filtered and filled in pipette bottles or other usual packings.

EXAMPLE 3

The Manufacture of Parenterally Applicable Cyclosporin A Forms of the Microemulsion Type The microemulsion preconcentrates described in Example 1.1 to 1.22 may serve as a basis for manufacturing injection or infusion solutions in that they are accordingly diluted with further additives such as physiological sodium chloride solution or 5% glucose solution and likewise.

| Example 3.1: Cylosporin A 0.25% infusion solution | |
|---|---|
| microemulsiom preconcentate according to Example 1.19 | 2.50% |
| 5% glucose solution | ad 100.00% |

The microemulsion preconcentrate is added under stirring at room temperature to the glucose solution. The resulting cyclosporin A O/W microemulsion is 0.2 μm sterile filtered and filled into usual sterile packagings.

EXAMPLE 4

| Example 4.1 Manufacture of an oral cyclosporin A placebo dosage form of the type microemulsion preconcentrate | |
|---|---|
| cyclosporin A (c) | 0.00% |
| Miglyol 812 (a1) | 40.00% |
| oleic acid (a2) | 15.00% |
| Tween 80 (b1) | 33.75% |
| Cremophor RH 40 (b2) | 11.25% |

The components (a1), (a2), (b1) and (b2) are mixed under stirring, where appropriate under slight heating. The formed microemulsion preconcentrate is filled into a soft or hard gelatine capsule. Hard gelatine capsules are preferably sealed using the quasi seal method.

| Example 4.2 Manufacture of a cyclosporin A placebo O/W microemulsion pump spray for the topical application | |
|---|---|
| Microemulsion preconcentrate according to Example 4.1 | 5.00% |
| Na$_2$-EDTA | 0.10% |
| benzalkonium chloride | 0.01% |
| 10 mM phosphate buffer pH 6 | ad 100.00% |

The microemulsion preconcentrate is added under stirring at room temperature is added to the phosphate buffer, containing Na$_2$-EDTA and benzalkonium chloride. The resulting cyclosporin A-placebo O/W microemulsion, with a particle size diameter of 26.8±13.4 nm is filled into a pump spray. Instead of the pump spray also pressurised gas and aerolosol sprays are considered.

EXAMPLE 5

Example 5.1 Manufacture of an oral quercetin dosage form of the type microemulsion preconcentrate

| | |
|---|---|
| quercetin (c) | 1.00% |
| Miglyol 812 (a1) | 45.00% |
| oleic acid (a2) | 9.00% |
| Tween 80 (b1) | 45.00% |

The components (a1), (a2), (b1) are mixed under stirring (e.g. magnetic stirring apparatus) at room temperature. In the resulting clear fluid quercetin is dissolved under stirring (e.g. magnetic stirring apparatus) at room temperature. The formed microemulsion preconcentrate is filled into a soft or hard gelatine capsule. Hard gelatine capsules are preferably sealed using the quasi seal method.

Example 5.2 Manufacture of a quercetin O/W microemulsion pump spray for the topical application

| | |
|---|---|
| Microemulsion preconcentrate according to Example 5.1 | 10.00% |
| Na$_2$-EDTA | 0.10% |
| Benzalkonium chloride | 0.01% |
| 10 mM phosphate buffer pH 6 | ad 100.00% |

The microemulsion preconcentrate is added under stirring at room temperature is added to the phosphate buffer, containing Na$_2$-EDTA and benzalkonium chloride. The resulting quercetin O/W microemulsion, with a particle size diameter of 34.1±15.5 nm is filled into a pump spray. Instead of the pump spray also pressurised gas and aerosol sprays are considered.

EXAMPLE 6

Microemulsion Preconcentrates

Example 6.1

| | |
|---|---|
| Miglyol 812 (a1) | 40.00% |
| oleic acid (a2) | 15.00% |
| Tween 80 (b1) | 33.75% |
| Cremophor RH 40 (b2) | 11.25% |

The components a1, a2, b1 and b2 are mixed under stirring (e.g. magnetic stirring apparatus), optionally under slight heating.

In an analogous manner also the following microemulsion preconcentrates may be manufactured:

Example 6.2

| | |
|---|---|
| Miglyol 812 (a1) | 40.00% |
| oleic acid (a2) | 15.00% |
| Tween 80 (b1) | 33.75% |
| Cremophor EL (b2) | 11.25% |

Example 6.3

| | |
|---|---|
| Miglyol 812 (a1) | 45.00% |
| oleic acid (a2) | 10.00% |
| Tween 80 (b1) | 33.75% |
| Cremophor EL (b2) | 11.25% |

Example 6.4

| | |
|---|---|
| Miglyol 812 (a1) | 50.00% |
| oleic acid (a2) | 5.00% |
| Tween 80 (b1) | 33.75% |
| Cremophor EL (b2) | 11.25% |

Example 6.5

| | |
|---|---|
| Miglyol 812 (a1) | 45.00% |
| oleic acid (a2) | 10.00% |
| Cremophor EL (b2) | 45.00% |

Example 6.6

| | |
|---|---|
| Miglyol 812 (a1) | 50.00% |
| oleic acid (a2) | 5.00% |
| Tween 80 (b) | 45.00% |

The microemulsion preconcentrates described in example 1.1 to 1.6 thereafter serve as a basis for the manufacture of O/W emulsions.

The invention claimed is:

1. A composition in the form of a microemulsion preconcentrate, comprising
   (a) a mixture consisting of (i) a fatty acid triglyceride, in which the fatty acid is caprylic acid or capric acid, and (ii) an omega-9 fatty acid and/or an omega-6 fatty acid; and
   (b) 20 to 80 percent by weight of a surface-active component, containing a tenside of the polyoxyethylene type which is essentially free of components mixable with water or components soluble in water, wherein the components comprise esterification products of polycarboxylic acids with 2-10 carboxyl groups with C1-C10 alcohols, and esterification products of polyols with 2-10 hydroxy groups with C2-C11 carboxylic acids.

2. A composition in the form of a microemulsion obtained by contacting a microemulsion preconcentrate as recited in claim 1 with water or an aqueous medium.

3. A composition according to claim 2, wherein the composition is an oil-in-water microemulsion having an average particle size less than 150 nm.

4. A composition according to claim 3, wherein said particle size is less than 100 nm.

5. A composition according to claim 2, comprising an active ingredient soluble in water.

6. A composition according to claim 1, wherein the omega-9 fatty acid and/or the omega-6 fatty acid comprises 12-24 C-atoms.

7. A composition according to claim 1, wherein the omega-9 fatty acid and/or the omega-6 fatty acid comprises 16-24 C-atoms.

8. A composition according to claim 1, wherein the omega-9 fatty acid and/or the omega-6 fatty acid comprises 18-22 C-atoms.

9. A composition according to claim 8, wherein the omega-9 fatty acid is oleic acid.

10. A composition according to claim 8, wherein the omega-6 fatty acid is linoleic acid.

11. A composition according to claim 1, wherein the weight ratio of component (ii) to said triglyceride is 1:1 to 1:200.

12. A composition according to claim 11, wherein said ratio is 1:2 to 1:20.

13. A composition according to claim 1, wherein the surface-active component (b) comprises a polyoxyethylene sorbitane fatty acid ester, a polyoxyethylene-glycolated natural or hydrated vegetable oil or mixtures thereof.

14. A composition according to claim 1, wherein the component (a) is present in a quantity of 20 to 70 percent by weight with respect to the total weight of the composition.

15. A composition according to claim 1, comprising as component (c) an active ingredient which is soluble in component (a) and/or component (b).

16. A composition according to claim 15, wherein the active ingredient is selected from the group of active ingredients which are not soluble or poorly soluble in water but soluble in component (a) and/or component (b).

17. A composition according to claim 15, wherein c) is coenzyme Q10.

18. A composition according to claim 15, wherein said active ingredient is selected from the group consisting of a pharmaceutical active ingredient, a biotechnological active ingredient, a cosmetic active ingredient, a foodstuff active ingredient and a cell or tissue culture active ingredient, and mixtures thereof.

19. A unit dosage form for administering an active ingredient, comprising a composition according to claim 1 or 15.

20. A unit dosage form according to claim 19, comprising a biopolymer.

21. A unit dosage form according to claim 19, wherein the biopolymer is gelatine.

22. A unit dosage form according to claim 19, comprising coenzyme Q10 as component (c).

* * * * *